US008529983B2

(12) United States Patent
Doshi et al.

(10) Patent No.: US 8,529,983 B2
(45) Date of Patent: Sep. 10, 2013

(54) METHOD AND SYSTEM FOR COATING INSERTABLE MEDICAL DEVICES

(75) Inventors: Manish Doshi, Surat (IN); Divyesh Sherdiwala, Surat (IN); Prakash Sojitra, Surat (IN); Ashwin Vyas, Amreli (IN); Pankaj Gandhi, Surat (IN); Bhavesh Chevli, Surat (IN); Yavar Pothiawala, Surat (IN)

(73) Assignee: Envision Scientific Pvt. Ltd., Surat (IN)

( * ) Notice: Subject to any disclaimer, the term of this patent is extended or adjusted under 35 U.S.C. 154(b) by 0 days.

(21) Appl. No.: 12/920,825

(22) PCT Filed: May 21, 2010

(86) PCT No.: PCT/IN2010/000351
§ 371 (c)(1),
(2), (4) Date: Sep. 2, 2010

(87) PCT Pub. No.: WO2011/086569
PCT Pub. Date: Jul. 21, 2011

(65) Prior Publication Data
US 2012/0276280 A1 Nov. 1, 2012

(30) Foreign Application Priority Data
Jan. 18, 2010 (IN) ............................ 132/MUM/2010

(51) Int. Cl.
*A61L 33/00* (2006.01)
(52) U.S. Cl.
USPC .......... 427/2.25; 427/2.24; 427/2.1; 427/294; 427/295; 427/296; 427/346; 427/350; 427/355
(58) Field of Classification Search
USPC .................. 427/2.4, 2.5; 118/500, 621, 503, 118/504, 320; 600/505, 549, 561
See application file for complete search history.

(56) References Cited

U.S. PATENT DOCUMENTS

| 6,565,659 | B1 | 5/2003 | Pacetti et al. |
| 7,628,859 | B1 | 12/2009 | Hossainy et al. |
| 2003/0059520 | A1 | 3/2003 | Chen et al. |
| 2004/0191405 | A1* | 9/2004 | Kerrigan ............... 427/2.24 |
| 2009/0181160 | A1 | 7/2009 | Pacetti |
| 2010/0040766 | A1 | 2/2010 | Chappa et al. |

FOREIGN PATENT DOCUMENTS

CN 101616644 12/2009

OTHER PUBLICATIONS

"International Search Report dated Dec. 2, 2010", PCT Application No. PCT/IN2010/000351, 4 pages.

* cited by examiner

*Primary Examiner* — Dah-Wei Yuan
*Assistant Examiner* — Andrew Bowman
(74) *Attorney, Agent, or Firm* — Timberline Patent Law Group PLLC

(57) ABSTRACT

A coating system for coating an Insertable Medical Device (IMD) with one or more drugs is disclosed. The coating system includes a spray nozzle unit for coating the IMD with one or more drugs. The IMD includes a guiding member, a coating member and a supporting member. The IMD is passed through a protection tube such that the guiding member is located within the protection tube and an end of the supporting member is connected to a holder to expose the coating member of the IMD to the spray nozzle unit. The protection tube is received by a mandrel fixture which includes a circular disc for holding and rotating the protection tube and the IMD within the protection tube. When the protection tube along with the IMD is rotated, the spray nozzle unit coats the coating member of the IMD with the one or more drugs.

4 Claims, 3 Drawing Sheets

METHOD AND SYSTEM FOR COATING INSERTABLE MEDICAL DEVICES

FIELD OF THE INVENTION

The invention generally relates to coating Insertable Medical Devices (IMD) with one or more drugs. More specifically, the invention relates to a method and system for coating a pre-crimped stent with the one or more drugs.

BACKGROUND OF THE INVENTION

Coating of Insertable Medical Devices (IMD) with drug remains a challenge. Generally, IMD such as a stent, a balloon and, stent and balloon assembly is coated with drug particles using various methods such as atomization, dipping, Chemical Vapor Deposition (CVD), using a drug brush etc. Similar methods are used for coating balloon-catheter assemblies.

In case of atomization, a stent is fixed to a mandrel fixture and the mandrel fixture is rotated. A spray gun nozzle deposits drug particles on the rotating stent. Further, in the case of CVD, a stent is held stationary in a vapor chamber containing drug particles suspended in a vapor medium. However, in these methods, inner and outer surfaces of the stent are coated with drug particles. Thereafter, a balloon-catheter assembly is coated using any of the above-mentioned methods and then the stent is crimped to the balloon in the balloon-catheter assembly.

In scenarios where the stent is pre-crimped to a balloon-catheter assembly, generally, the CVD method is used to coat the pre-crimped stent. However, the drug particles are not uniformly deposited on the pre-crimped stent using this method.

Therefore, there is a need in the art for a method and system for efficiently coating a pre-crimped stent with drug particles. Further, there is a need in the art for methods for using a spray gun nozzle to coat a pre-crimped stent with drug particles.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the invention.

Figure 1A:
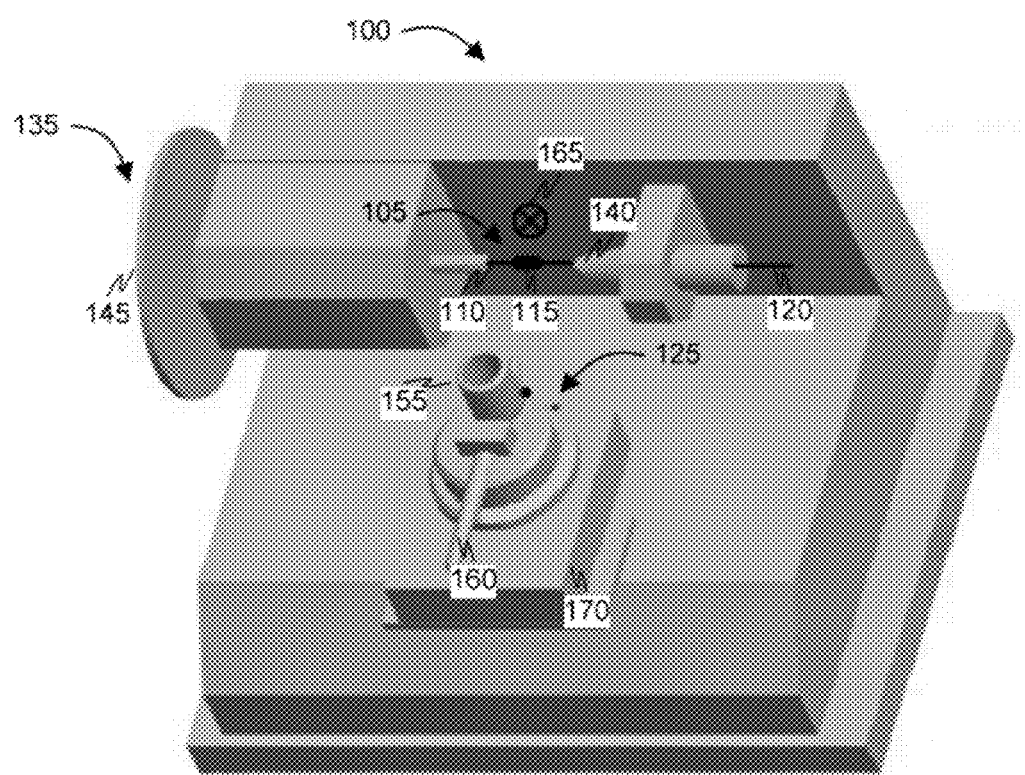
FIG. 1A illustrates an exemplary representation of a perspective view of a coating system for coating an IMD with one or more drugs in accordance with various embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION OF THE INVENTION

Before describing in detail embodiments that are in accordance with the invention, it should be observed that the embodiments reside primarily in combinations of method steps and apparatus components related to method and system for coating an Insertable Medical Device (IMD) with one or more drugs. Accordingly, the apparatus components and method steps have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Various embodiments of the invention provide methods and a coating system for coating an Insertable Medical Device (IMD) with one or more drugs. The coating system includes a spray nozzle unit for coating the IMD with one or more drugs. The IMD includes a guiding member, a coating member and a supporting member. The IMD is passed through a protection tube such that the guiding member is located within the protection tube and an end of the supporting member is connected to a holder to expose the coating member of the IMD to the spray nozzle unit. The protection tube is received by a mandrel fixture which includes a circular disc for holding and rotating the protection tube and the IMD within the protection tube. Thereafter, when the protection tube and the IMD is rotated, the spray nozzle unit coats the coating member of the IMD with the one or more drugs.

Figure 1B:
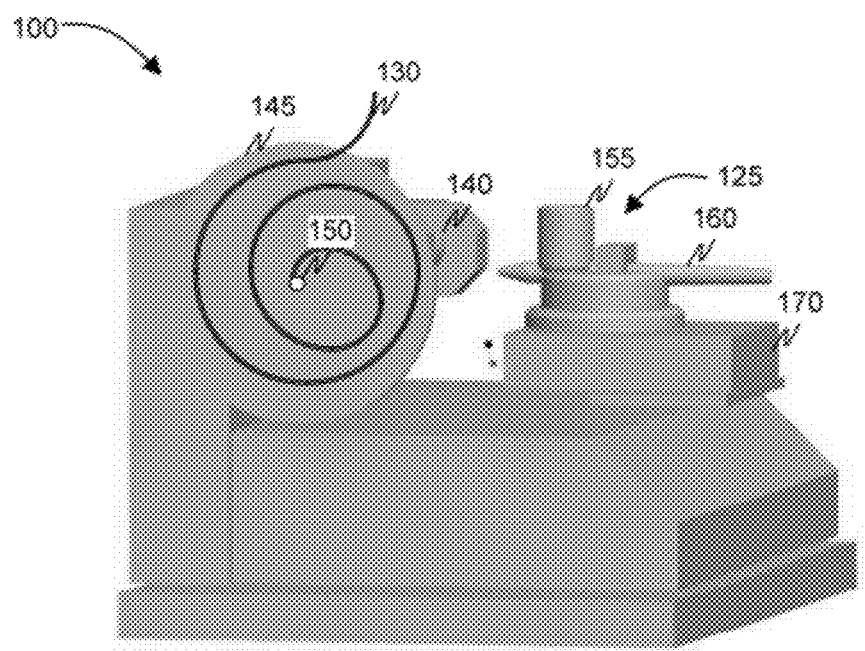
FIG. 1B illustrates a flow diagram of a left view of the coating system 100 for coating an IMD with one or more drugs.

FIG. 1A and FIG. 1B illustrate a perspective view and a left view, respectively, of a coating system 100 for coating an IMD 105 with one or more drugs. Examples of IMD 105 may include but are not limited to, a pre-crimped stent assembly and a balloon assembly. IMD 105 includes a guiding member 110, a coating member 115 and a supporting member 120. Considering the case where, IMD 105 is a pre-crimped stent assembly, guiding member 110 may be a catheter tube. Further, the coating member may be a stent pre-crimped to a balloon. Coating system 100 includes a spray nozzle unit 125, a protection tube 130, a mandrel fixture 135 and a holder 140. Spray nozzle unit 125 is used for coating the one or more drugs on coating member 115 of IMD 105.

Protection tube 130 as shown in FIG. 1B holds IMD 105. More specifically, IMD 105 is guided through protection tube 130 such that guiding member 110 is located within protection tube 130 and an end of supporting member 120 and coating member 115 protrudes out of protection tube 130. Thus, coating member 115 is exposed to spray nozzle unit 125 as shown in FIG. 1A and FIG. 1B.

Protection tube 130 holding IMD 105 is received by mandrel fixture 135 to mount protection tube 130 holding IMD 105 on coating system 100 shown in FIG. 1A. Mandrel fixture 135 includes a circular disc 145 and a guide hole 150 for holding protection tube 130 along with IMD 105 as shown in FIG. 1A and FIG. 1B. Guide hole 150 receives protection tube 130 along with IMD 105. On end of protection tube 130 is connected to circular disc 145.

In an embodiment, the one end of protection tube 130 may be fixedly coupled to circular disc 145. Further, other end of protection tube 130 may be guided through guide hole 150 of mandrel fixture 135. Protection tube 130 is passed through guide hole 150 located at the center of circular disc 145. Thereafter, IMD 105 may be passed through protection tube 130 such that supporting member 120 and coating member 115 protrudes out of protection tube 130 as shown in FIG. 1A. Alternatively, protection tube 130 may be coiled and the one end of protection tube 130 may be fixedly coupled to circular disc 145. Thereafter, the other end of protection tube 130 may be passed through guide hole 150 of mandrel fixture 135.

In another embodiment, protection tube 130 preloaded with IMD 105 may have one end fixedly attached to circular disc 145. Further, the other end of protection tube 130 may be passed through guide hole 150 thereby enabling mandrel fixture 135 to hold protection tube 130 along with IMD 105. Thereafter, an end of supporting member 120 that protrudes out of protection tube 130 is connected to holder 140 of coating system 100. Circular disc 145 holds protection tube 130 and rotates the protection tube along with IMD 105. When protection tube 130 along with IMD 105 is rotated, spray nozzle unit 125 coats coating member 115 of IMD 105 with the one or more drugs in a uniform manner.

Spray nozzle unit 125 includes a feed cup 155 as illustrated in FIG. 1B. Feed cup 155 supplies a drug solution including the one or more drugs and a solvent to spray nozzle unit 125. In an embodiment of the invention, a pump (not shown in FIG. 1A and FIG. 1B) is used to supply the drug solution to feed cup 155. Examples of the pump may include, but not limited to a syringe pump, a gear pump, a centrifugal pump and a gravity pump. The pump supplies the drug solution to feed cup 155 at a controlled pressure. The pump may be controlled using one or more of, but not limited to a Computer Numerical Control (CNC) and an electric controller. Spray nozzle unit 125 further includes an atomizer unit 160. Atomizer unit 160 receives the drug solution from feed cup 155. An inert gas is passed through atomizer unit 160 to atomize the drug solution. The atomized drug solution is then sprayed on coating member 115 to coat coating member 115 of IMD 105 with the one or more drugs. The atomized drug solution is sprayed on coating member 115 of IMD 105. In an embodiment, one or more layers of the one or more drugs may be coated on coating member 115. For example, coating member 115 may be coated with multiple layers of different drug compositions by spray nozzle unit 125 of coating system 100. These drug compositions may be selected based on the therapeutic needs.

In an embodiment, atomizer unit 160 may be capable of nanomizing the one or more drugs. In this case, a nano drop of the drug solution present in feed cup 155 is converted into nanoparticles by atomizer unit 160. The flow of the drug solution from feed cup 155 to spray nozzle unit 125 is controlled by but not limited to, a CNC. The nano drop of the drug solution comes in contact with the inert gas present in spray nozzle unit 125 to form the nanoparticles of the one or more drugs present in the drug solution. Thereafter, these nanoparticles of the one or more drugs are coated on coating member 115 of IMD 105.

While spraying the atomized or nanomized drug solution, the solvent in the drug solution evaporates and the one or more drugs in the drug solution are coated on coating member 115 of IMD 105. In an embodiment, an air blower 165 of coating system 100 may be used to increase the rate of evaporation of the solvent in the drug solution as shown in FIG. 1A.

For example, when drug particles of the drug solution are sprayed on coating member 115, the solvent present in these drug particles evaporate when these drug particles travel from spray nozzle unit 125 to a surface of coating member 115. This evaporation of the solvent, increases concentration of the one or more drugs near to the surface of coating member 115. When the atomized or nanomized drug solution is sprayed on coating member 115 of IMD 105, pressure associated with the drug particles may be adjusted such that the drug particles impinges on surface of coating member 115. The drug particles impinges on the surface of coating member 115 due to a pressure gradient developed between spray nozzle unit 125 and a surface of coating member 115. The pressure gradient is developed when a stream of the drug particles has a higher concentration near to the surface of coating member 115 and subsequently the stream of the drug particles is forced by other incoming stream of drug particles having lower concentration of drugs.

In an embodiment, atomizer unit 160 may release the drug particles after predefined time intervals. Therefore, during each predefined time interval, the drug particles coated on the surface of coating member 115 dries. Further, during this predefined time interval, the pump does not supply the drug solution to atomizer unit 160.

Spray nozzle unit 125 may be mounted on a movable platform 170 of coating system 100 shown in FIG. 1A and FIG. 1B. Movable platform 170 enables movement of spray nozzle unit 125 in a plurality of directions. For example, spray nozzle unit 125 may be moved along one or more of an X axis, a Y axis and a Z axis. Such movement enables spray nozzle unit 125 to coat the one or more drugs on coating member 115 of IMD 105 uniformly.

In an embodiment of the invention, the movement of spray nozzle unit 125 may be controlled by a Computer Numerical Control (CNC). In such a case, spray nozzle unit 110 is guided to move along the plurality of directions by the CNC to coat a required concentration of the one or more drug particles on coating member 115 exposed to spray nozzle unit 125. Moreover, as spray nozzle unit 110 is controlled by the CNC, the movement of spray nozzle unit 125 may be accurate thereby facilitating spray nozzle unit 125 to coat the one or more drug particles in the uniform manner.

During operation, spray nozzle unit 125 moves in the plurality of directions synchronously with a rotational motion of protection tube 130 along with IMD 115. Due to the movement of spray nozzle unit 125 and protection tube 130 along with IMD 115, an amount of the one or more drugs coated on coating member 115 of IMD 105 coated in a middle portion of coating member 115 is more as compared to an amount of the one or more drugs coated on either side portions of coating member 115.

Figure 2:
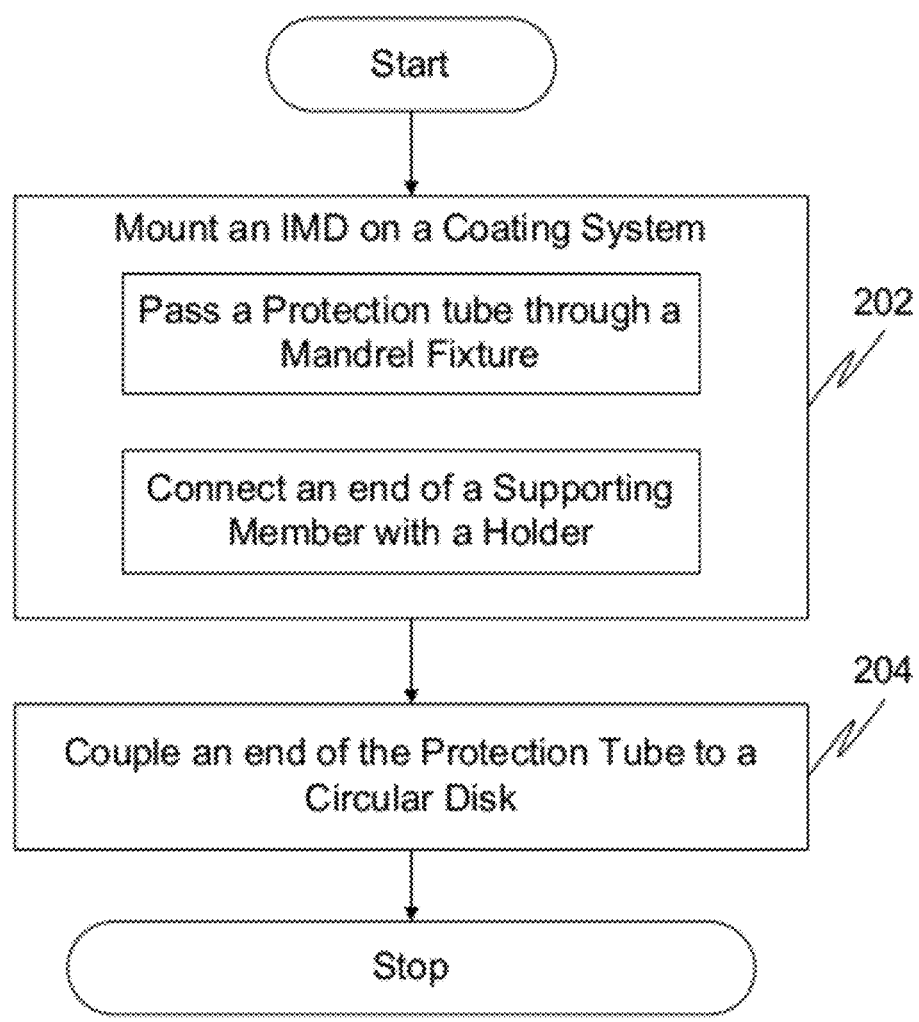
FIG. 2 illustrates a block diagram of a method for installing an IMD on a coating system for coating one or more drugs on the IMD.

FIG. 2 illustrates a method for installing an IMD on a coating system for coating one or more drugs on the IMD. The coating system includes a spray nozzle unit, a protection tube holding the IMD and a mandrel fixture. The IMD is guided through the protection tube for enabling the protection tube to hold the IMD. The IMD includes a guiding member, a coating member and a supporting member. When the IMD is held by the protection tube, the guiding member is located within the protection tube. Further, the coating member and the supporting member of the IMD protrude out of the protection tube thereby exposing the coating member to the spray nozzle unit.

At step 202, the IMD is mounted on the coating system for coating the IMD with the one or more drugs. For mounting the IMD, initially the protection tube holding the IMD is passed through the mandrel fixture in a manner such that the guiding member of the IMD is located within the protection tube and the coating member along with the supporting member protrudes out from the protection tube. Thereafter, an end of the supporting member is connected to a holder on the coating system. Thus, the coating member of the IMD is exposed to the spray nozzle unit for coating the coating member of the IMD with one or more drugs.

Subsequently, at step 204, an end of the protection tube holding the IMD is coupled to a circular disc on the mandrel fixture. Thereafter, an end of the supporting member is connected to the holder thereby installing the protection tube holding the IMD in the coating system. In an embodiment of the invention, the protection tube is coupled to the circular disc and thereafter, the IMD is inserted into the protection tube, thus enabling the protection tube to hold the IMD. The protection tube may also be coiled to the circular disc.

During operation, the circular disc rotates the protection tube along with the IMD. While rotating the protection tube along with the IMD, the coating member of the IMD is exposed to the spray nozzle unit. The spray nozzle unit then coats the one or more drugs on the coating member. The method of coating the one or more drugs is explained in detail in conjunction with FIG. 1A and FIG. 1B.

Various embodiments of the invention provide methods and a coating system for coating an Insertable Medical Device (IMD) with one or more drugs. The coating system includes a mandrel fixture capable of receiving a protection tube holding an Insertable Medical Device (IMD) such as, a precrimped stent. Further, a spray nozzle unit of the coating system used for coating one or more drugs on the IMD is Computer Numerical Control (CNC) controlled thereby enabling the one or more drugs to be coated in a uniform manner due efficient control of distance between the spray nozzle unit and a surface of the coating member. The spray nozzle unit is capable of coating the IMD with nanoparticles of the one or more drugs. As result, the process of coating the one or more drugs is more efficient and better controlled. Further, an exhaust fan present in the coating system reduces the time associated with drying of the one or more drugs coated on the IMD.

Those skilled in the art will realize that the above recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method of installing an Insertable Medical Device (IMD) on a coating system for coating at least one drug on the IMD, the method comprising:
   mounting the IMD in the coating system, the coating system comprising a spray nozzle unit, a protection tube holding the IMD and a mandrel fixture, the IMD having a guiding member, a coating member and a supporting member, wherein mounting the IMD comprises:
      passing the protection tube holding the IMD through the mandrel fixture, wherein the guiding member of the IMD is located within the protection tube and the coating member along with the supporting member protrudes out from the protection tube, and
      connecting an end of the supporting member with a holder thereby exposing the coating member to the spray nozzle unit for coating the at least one drug on the coating member of the IMD; and
   coupling an end of the protection tube to a circular disc of the mandrel fixture for installing the IMD.

2. The method of claim 1, wherein the coating member of the IMD is one of:
   a pre-crimped stent member, the pre-crimped stent member comprising,
      a balloon, and
      a stent crimped onto the balloon; and
   a balloon.

3. The method of claim 1 further comprising inserting the IMD into the protection tube thereby enabling the protection tube to hold the IMD.

4. The method of claim 1, wherein the end of the protection tube is fixedly coupled to the circular disc, the protection tube is coiled.

* * * * *